United States Patent [19]

Covey et al.

[11] Patent Number: 5,019,152

[45] Date of Patent: May 28, 1991

[54] SUBSTITUTED TETRAZOLINONES AND THEIR USE AS HERBICIDES

[75] Inventors: Rupert A. Covey, Bethany; Patricia Forbes, Waterbury; Allyn R. Bell; Allen R. Blem, both of Cheshire, all of Conn.

[73] Assignee: Uniroyal Chemical Company, Inc., Middlebury, Conn.

[21] Appl. No.: 548,151

[22] Filed: Jul. 5, 1990

Related U.S. Application Data

[60] Division of Ser. No. 282,424, Dec. 9, 1988, which is a division of Ser. No. 860,712, May 7, 1986, Pat. No. 4,830,661, which is a continuation-in-part of Ser. No. 737,371, May 23, 1985, Pat. No. 4,826,529, which is a continuation-in-part of Ser. No. 560,031, Dec. 9, 1983, Pat. No. 4,618,365.

[51] Int. Cl.$^5$ .................... A01N 43/48; A01N 43/64; A01N 43/713

[52] U.S. Cl. .................................. 71/92; 71/76; 548/251

[58] Field of Search ........................... 71/92; 548/251

[56] References Cited

U.S. PATENT DOCUMENTS

| 3,865,570 | 2/1975 | George | 71/76 |
| 3,925,054 | 12/1975 | Krenser | 71/92 |
| 4,404,019 | 9/1983 | Uematsu et al. | 71/92 |

FOREIGN PATENT DOCUMENTS

| 8501939 | 5/1985 | PCT Int'l Appl. | 71/92 |

OTHER PUBLICATIONS

Tsuge et al., "Reactions of Trimethylsilyl Azide with Heterocumulenes", Journal of Organic Chemistry, vol. 45, No. 25 (1980), pp. 5130–5136.

Elderfield et al., Heterocyclic Compounds, vol. 8, Wiley and Sons, N.Y., N.Y., 1967, p. 84.

*Primary Examiner*—Allen J. Robinson
*Assistant Examiner*—John D. Pak
*Attorney, Agent, or Firm*—Raymond D. Thompson

[57] ABSTRACT

Substituted tetrazolinones exhibit usefulness as herbicides and plant growth regulators.

2 Claims, No Drawings

SUBSTITUTED TETRAZOLINONES AND THEIR USE AS HERBICIDES

This is a division of application Ser. No. 282,424 filed Dec. 9, 1988 which is a division of application Ser. No. 860,712 now U.S. Pat. No. 4,830,661, filed May 7, 1986, which is a continuation-in-art of application Ser. No. 737,371 now U.S. Pat. No. 4,826,529 filed May 23, 1985 which is a continuation-in-part of application Ser. No. 560,031 filed Dec. 9, 1983 now U.S. Pat. No. 4,618,365.

BACKGROUND OF THE DISCLOSURE

1. Field of the Invention

The instant invention is directed to a new class of substituted tetrazolinone compounds. More specifically, the instant invention relates to a new class of substituted tetrazolinone compounds which are useful as herbicides and/or as plant growth regulators.

2. Background of the Prior Art

The synthesis of certain substituted tetrazolinones is known in the art. Thus, Horwitz, et al, JACS, 81 3076 (1959) and Tsuge et al, J. Org. Chem., 45 5130 (1980) provide methods for synthesizing tetrazolinones. These disclosures provide no utility for the classes of substituted tetrazolinones synthesized.

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weed control is essential for maximum production of many agronomic and horticultural crops including corn, (Zea mays L.), cotton (Gossypium SP), sunflower (Helianthus annus L.) and soybeans (Glycine max (L.) Merr.). Weeds on noncropped areas may cause a fire hazard, undesirable drifting of sand or snow, and/or irritation to persons with allergies. Thus, suppression of undesirable weed growth is very advantageous.

Moreover, the need for agricultural chemicals having significant effects on the growth and development of crop plant species is similarly well known. Thus, for many crops, it is highly desirable that certain plant growth regulatory effects by accomplished. In general, these growth regulatory effects include one or more of the following: dwarfing, cessation of terminal growth, inhibition or stimulation of axillary and intercalary growth, retardation or stimulation of internode elongation, inhibition or stimulation of flowering or reproductive development, and the like.

SUMMARY OF THE INVENTION

It has now been found that a new class of substituted tetrazolinones unexpectedly provides excellent herbicidal properties and plant growth regulatory effects.

In accordance with the instant invention, a compound having the formula:

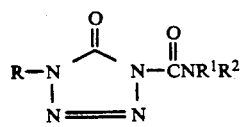

wherein R is:
C$_1$-C$_{12}$ alkyl,
C$_2$-C$_{13}$ alkoxyalkyl,
C$_7$-C$_9$ aralkyl,
C$_5$-C$_6$ cycloalkyl,
C$_3$-C$_{12}$ alkenyl,
naphthyl,
phenyl,
phenyl substituted with at least one member selected from the group consisting of:
fluorine,
chlorine,
bromine,
iodine,
C$_1$-C$_4$ alkyl,
C$_1$-C$_4$ alkoxy,
methylenedioxy,
NR$^3$R$^4$ wherein R$^3$ and R$^4$ are the same or different and are hydrogen or C$_1$-C$_6$ alkyl,
C$_2$-C$_5$ alkoxycarbonyl,
carboxy,
phenoxy,
nitro,
cyano,
trihalomethyl wherein halo is fluorine, chlorine or bromine,
trihalomethoxy wherein halo is fluorine, chlorine or bromine,
C$_1$-C$_6$ alkylthio, and
C$_1$-C$_6$ fluoroalkylthio; or benzyl substituted with at least one member selected from the group consisting of:
fluorine,
chlorine,
bromine,
iodine,
C$_1$-C$_4$ alkyl,
C$_1$-C$_4$ alkoxy,
methylenedioxy,
C$_2$-C$_5$ alkoxycarbonyl,
phenoxy,
nitro,
cyano,
trihalomethyl wherein halo is fluorine, chlorine or bromine,
trihalomethoxy wherein halo is fluorine, chlorine or bromine,
C$_1$-C$_6$ alkylthio, and
C$_1$-C$_6$ fluoroalkylthio;
R$^1$ is selected from the group consisting of:
C$_1$-C$_6$ alkyl,
C$_3$-C$_6$ alkenyl,
C$_5$-C$_6$ cycloalkyl,
C$_7$-C$_9$ aralkyl,
C$_7$-C$_9$ aralkyl substituted with at least one member selected from the group consisting of:
fluorine,
chlorine,
bromine,
iodine,
C$_1$-C$_6$ alkyl,
C$_1$-C$_2$ haloalkyl wherein halo is fluorine, chlorine or bromine,
halomethoxy wherein halo is fluorine, chlorine or bromine,
C$_1$-C$_6$ alkoxy,
C$_1$-C$_6$ alkylthio,
C$_1$-C$_6$ fluoroalkylthio,
phenoxy,
phenylthio,
carboxy, C₂-C₅ alkoxycarbonyl,
nitro,
cyano, and
NR⁷R⁸ wherein R⁷ and R⁸ are the same or different and are hydrogen, C₁-C₆ alkyl, C₄-C₈ alkylene or C₄-C₈ oxydialkylene; or
naphthyl,
phenyl, and
phenyl substituted with at least one member selected from the group consisting of:
fluorine,
chlorine,
bromine,
iodine,
C₁-C₆ alkyl,
C₁-C₂ haloalkyl wherein halo is fluorine, chlorine or bromine:
halomethoxy wherein halo is fluorine, chlorine or bromine,
C₁-C₆ alkoxy,
C₁-C₆ alkylthio,
C₁-C₆ fluoroalkylthio,
phenoxy,
phenyl,
phenylthio,
carboxy,
C₂-C₅ alkoxycarbonyl,
nitro,
cyano, and
NR⁷R⁸ wherein R⁷ and R⁸ are the same or different and are hydrogen, C₁-C₆ alkyl, C₄-C₈ alkylene or C₄-C₈ oxydialkylene: and
R² is a radical having the formula:

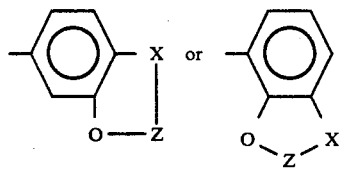

wherein X is oxygen or CH₂, and
Z is —CH₂—CH₂ or —CR⁹R¹⁰— wherein R⁹ and R¹⁰ are the same or different and are hydrogen or methyl,
is disclosed.

In further accordance with the instant invention a composition is provided comprising the compound of this invention with a carrier.

In still further accordance with the present invention a method for controlling weeds and undesirable vegetation employing the composition of this invention is taught.

In yet further accordance with the present invention, a method for regulating the growth of plants employing the composition of this invention is taught.

DETAILED DESCRIPTION

The present invention is directed to a compound having the structural formula:

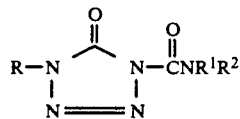

wherein R is:
C₁-C₁₂ alkyl,
C₂-C₁₃ alkoxyalkyl,
C₇-C₉ aralkyl,
C₅-C₆ cycloalkyl,
C₃-C₁₂ alkenyl,
naphthyl,
phenyl,
phenyl substituted with at least one member selected from the group consisting of:
fluorine,
chlorine,
bromine,
iodine,
C₁-C₄ alkyl,
C₁-C₄ alkoxy,
methylenedioxy,
NR³R⁴ wherein R³ and R⁴ are the same or different and are hydrogen or C₁-C₆ alkyl,
C₂-C₅ alkoxycarbonyl,
carboxy,
phenoxy,
nitro,
cyano,
trihalomethyl wherein halo is fluorine, chlorine or bromine,
trihalomethoxy wherein halo is fluorine, chlorine or bromine,
C₁-C₆ alkylthio, and
C₁-C₆ fluoroalkylthio; or
benzyl substituted with at least one member selected from the group consisting of:
fluorine,
chlorine,
bromine,
iodine,
C₁-C₄ alkyl,
C₁-C₄ alkoxy,
methylenedioxy,
C₂-C₅ alkoxycarbonyl,
phenoxy,
nitro,
cyano,
trihalomethyl wherein halo is fluorine, chlorine or bromine,
trihalomethoxy wherein halo is fluorine, chlorine or bromine,
C₁-C₆ alkylthio, and
C₁-C₆ fluoroalkylthio;
R¹ is selected from the group consisting of:
C₁-C₆ alkyl,
C₃-C₆ alkenyl,
C₅-C₆ cycloalkyl,
C₇-C₉ aralkyl,
C₇-C₉ aralkyl substituted with at least one member selected from the group consisting of:
fluorine,
chlorine,
bromine,
iodine,
C₁-C₆ alkyl,
C₁-C₂ haloalkyl wherein halo is fluorine, chlorine or bromine;
halomethoxy wherein halo is fluorine, chlorine or bromine,
C₁-C₆ alkoxy,
C₁-C₆ alkylthio,
C₁-C₆ fluoroalkylthio, phenoxy,
phenylthio,
carboxy,
$C_2$-$C_5$ alkoxycarbonyl,
nitro,
cyano, and
$NR^7R^8$ wherein $R^7$ and $R^8$ are the same or different and are hydrogen, $C_1$-$C_6$ alkyl, $C_4$-$C_8$ alkylene or $C_4$-$C_8$ oxydialkylene;

naphthyl,
phenyl, and
phenyl substituted with at least one member selected from the group consisting of:
fluorine,
chlorine,
bromine,
iodine,
$C_1$-$C_6$ alkyl,
$C_1$-$C_2$ haloalkyl wherein halo is fluorine, chlorine or bromine;
halomethoxy wherein halo is fluorine, chlorine or bromine,
$C_1$-$C_6$ alkoxy,
$C_1$-$C_6$ alkylthio,
$C_1$-$C_6$ fluoroalkylthio,
phenoxy,
phenyl,
phenylthio,
carboxy,
$C_2$-$C_5$ alkoxycarbonyl,
nitro,
cyano, and
$NR^7R^8$ wherein $R^7$ and $R^8$ are the same or different and are hydrogen, $C_1$-$C_6$ alkyl, $C_4$-$C_8$ alkylene or $C_4$-$C_8$ oxydialkylene; and
$R^2$ is a radical having the formula:

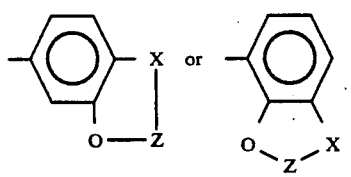

wherein X is oxygen or $CH_2$, and
Z is $-CH_2-CH_2-$ or $-CR^9R^{10}-$ wherein $R^9$ and $R^{10}$ are the same or different and are hydrogen or methyl.

Among the more preferred compounds of this invention are those wherein:
R is $C_1$-$C_4$ alkyl,
phenyl, or
phenyl substituted with at least one member of the group consisting of:
$C_1$-$C_3$ alkyl and
$C_1$-$C_3$ alkoxy:
$R_1$ is $C_1$-$C_4$ alkyl: and
$R_2$ is 3,4-methylenedioxyphenyl.

The compounds of this invention are prepared by reacting a tetrazolinone compound having the formula:

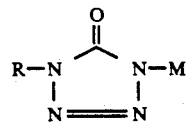 [I]

wherein M is hydrogen or alkali metal (such as Li, Na or K) and R is as defined above with a carbamoyl halide having the formula $QCONR^1R^2$, wherein Q is chlorine or bromine and $R^1$ and $R^2$ have the meanings above.

When M is hydrogen, the reaction is preferably conducted in the presence of a suitable acid acceptor such as pyridine or a tertiary amine (e.g., triethylamine). It is noted that this tetrazolinone compound may be synthesized by the methods disclosed in the Horwitz et al and Tsuge et al references mentioned above. The equivalent ratio of Q/M (as representative of the above reactants) may vary from about 0.75/1 to about 2/1, preferably from about 0.9/1 to about 1.5/1. Excess of M may be advantageous in the purification of product since the M-type tetrazolinone is soluble in base. The reaction temperature may range from about 40° C. to the boiling point of the solvent used. Typically, the reaction is conducted under reflux conditions. Suitable solvents are those which are inert to the reactant, such as acetone, acetonitrile, toluene, chloroform and the like. The reaction time may vary from several minutes or less to several hours or more depending on factors such as reaction batch size, reaction temperature, and the like.

Alternatively, the compounds of this invention may be prepared by reacting a tetrazolinone having the formula [I] above with phosgene, and then further reacting the product of such reaction with the appropriate secondary amine.

The instant invention is also directed to a composition comprising the substituted tetrazolinone compound of this invention and a carrier therefor. The carrier employed in one preferred embodiment of this invention is a finely-divided or granular inorganic or organic material such as attapulgite clay, sand, vermiculite, ground corn cobs, activated carbon and the like. The compound of this invention may be impregnated on the finely-divided or granular material.

The carrier may also be an inert powder. Preferably, the inert powder is one of the mineral silicates, e.g., mica, talc, pyrophyllite and clays. In this case, the composition is formed by grinding the compound of this invention into a fine powder and mixing it with the inert powder to which a surface active dispersing agent has been added.

A third carrier is the combination of the above inert powder and water. This carrier employs the wettable powder dispersed in water.

Yet another carrier is a solvent and water. In this embodiment the compound of this invention is dissolved in a solvent such as benzene, toluene or other aliphatic or aromatic hydrocarbon. An emulsifiable concentrate is formed with the addition of a surface active and/or dispersing agent. The emulsifiable concentrate is then dispersed in water. In this composition water solubility may be increased using a cosolvent system involving acetone, dimethyl sulfoxide or other water miscible solvent.

It is noted that the surface active agents preferred for use in the composition of this invention are well known to those skilled in the art. In addition, suitable surface active agents for use in the composition of this invention are provided in McCutcheon's Detergents and Emulsifiers, 1970, Allured Publishing Corp., Ridgewood, N.J.: U.S. Pat. No. 2,614,916, columns 2 to 4; and U.S. Pat. No. 2,547,727, columns 3 and 4.

The present invention is furthermore directed to a method of controlling weeds by application of a herbicidally effective amount of the composition of this invention.

In the case where the composition comprises impregnated granules of the compound of this invention, application, to control weeds, is by spreading on the soil. The wettable powder may be similarly applied. In the case where the wettable powder is dispersed in water, this composition controls weeds by spraying the dispersion onto the soil surface. Where an emulsion is formed that emulsion is likewise sprayed onto the soil surface.

When employed as a herbicide, the concentration of the compound of this invention in the composition of this invention may vary widely, e.g. from 1 to 95%. The concentration of active compound in dispersions applied to the soil or foliage is generally from 0.002% to about 75%.

For use as a pre-emergence herbicide the compound of this invention is typically applied at rates of from about 0.05 to about 25 pounds per acre (from about 0.056 to about 28 kg/ha) to soil which contains weed and crop seed, namely either to the surface of the soil or incorporated into the upper one to three inches (2.5 to 7.5 cm.) of soil. The compound may be employed singly or as a mixture of two or more chemicals.

When employed as a herbicide, the most suitable rate of application in any given case will depend on such factors as soil type, soil pH, soil organic matter content, the quantity and intensity of rainfall before and after treatment, the air and soil temperature, light intensity and light duration per day. All of these factors can have an influence on the efficacy of the chemicals for a given weed control use.

The herbicide use may include control of vegetation at industrial sites or selective weed control in crop fields.

In addition, the present invention is directed to a method of regulating the growth of plants by the application of a plant growth regulatory effective amount of the composition of this invention. It will be understood that the term plant, as used herein, includes plant parts such as foliage, roots, flower stems and seeds. Depending on the crop variety, dosage, time of application and certain cultural practices, the growth regulating effects which may be obtained include one or more of the following: dwarfing, cessation of terminal growth, inhibition of axillary and intercalary growth, retardation of internode elongation, inhibition of flowering or reproductive development, and the like.

Compounds of this invention may be used alone, or in combination with one or more pesticidal compositions, or in combination with one or more spray adjuvants (e.g. surface active agents, stickers, spreaders, emulsifiers, suspending agents, or extenders). The amount of active compound employed follows conventional practice for plant growth regulatory uses, and the chemicals are suitable applied as a formulation in accordance with conventional agricultural chemical practice.

The most suitable dosage of application of the active ingredient(s) for plant growth regulatory effects and the type and amount of adjuvant substances to be added to the spray solution will depend on a number of factors, including the plant species: the stage of plant development; the mode of application: the specific biological effect desired: the air and soil temperature: the quantity and intensity of rainfall before and after treatment; the soil type, pH, fertility and moisture and organic matter content; the physiological condition and vigor of the target plants; the relative humidity and wind velocity of the air around the crop; the extent and density of the foliar canopy of the target plant; the light quality, intensity and duration each day: the type and interval of previous and subsequent crop protectant chemical applications. All of these factors may have an influence on the efficacy of chemicals applied as plant growth regulators. However, one skilled in the art can, by routine experimentation, readily determine optimum conditions for the employment of any particular compound of this invention.

EXAMPLES

The following examples are given to illustrate the invention. Since these examples are illustrative of the invention, the invention should not be deemed to be limited thereto.

EXAMPLE 1

Preparation of 1-Ethyl-5(4H)tetrazolinone-4-carbonyl Chloride

A 23.3% phosgene solution in toluene (85.0 grams, 0.20 mole) was further diluted with 100 ml. of toluene and the solution was cooled to 10° C. A solution of 18.2 grams (0.16 mole) of 1-ethyl-5(4H)tetrazolinone, 23.3 ml. (17.0 grams, 0.168 mole) of triethylamine, 0.20 gram (0.0016 mole) of 4-dimethylaminopyridine and 70 ml. of toluene was added to the phosgene solution over a period of about 10 minutes keeping the reaction temperature below 28° C. The mixture was stirred for 0.5 hour and filtered to remove the precipitated salt. The filtrate was evaporated to dryness and finally warmed to 40° C. (0.2 mm) giving 20.5 grams of an oily solid. Recrystallization from toluene/hexane yielded 15.4 grams (55%) of a light-tan granular solid, m.p. 71°–76° C. The structure was confirmed by IR.

EXAMPLE 2

Preparation of 1-Ethyl-4-[N-(2-propyl)-N-(3,4-methylenedioxyphenyl)carbamyl]-5(4H)tetrazolinone (Compound No. 1)

1-ethyl-5(4H)tetrazolinone-4-carbonyl chloride (2.65 grams, 0.015 mole), 2.0 ml. of pyridine and 2.5 grams (0.014 mole) of N-(2-propyl)-3,4-methylenedioxyaniline were combined whereupon a slight exothermic reaction occurred. The reaction mixture was stirred for sixteen hours. The pyridine hydrochloride and the product precipitated from the mixture. Water was added to remove the salt, and the insoluble product was removed by filtration. Recrystallization from ethanol yielded 2.3 grams (52%) of white crystals, m.p. 93°–94° C.

The structure shown in Table I was confirmed by IR and NMR spectra.

TABLE I

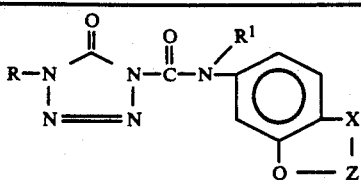

| Cpd. No. | R | R¹ | X | Z |
|---|---|---|---|---|
| 1 | $CH_3CH_2$ | $i$-$C_3H_7$ | O | $CH_2$ |

Following essentially the procedures outlined above additional compounds within the scope of this invention are prepared. These compounds, compounds 2-8, are defined in Table II.

TABLE II

| Cpd. No. | R | R¹ | X | Z |
|---|---|---|---|---|
| 2 | $CH_3$ | $i$-$C_3H_7$ | O | $CH_2$ |
| 3 | $C_6H_5$ | $i$-$C_3H_7$ | O | $CH_2$ |
| 4 | $CH_3CH_2$ | $CH_3$ | O | $CH_2$ |
| 5 | $CH_3CH_2$ | 2-butyl | O | $CH_2$ |
| 6 | $CH_3$ | $i$-$C_3H_7$ | $CH_2$ | $CH_2$ |
| 7 | $CH_3$ | $i$-$C_3H_7$ | $CH_2$ | $-CH_2CH_2-$ |
| 8 | $CH_3$ | $i$-$C_3H_7$ | $CH_2$ | $\begin{array}{c}-C-\\ /\ \backslash\\ CH_3\ \ CH_3\end{array}$ |

EXAMPLE 4

To illustrate the effectiveness of the previously described substituted tetrazolinones of this invention as pre-emergence herbicide, 300 mg of compound 1 was dissolved in a composition comprising 10 ml acetone to which 30 mg emulsifying agent, ethoxylated sorbitan monolaurate, was added. The solution was diluted to 100 ml with distilled water. Ten milliliters of this 3000 ppm solution was diluted to 250 ppm with distilled water. The chemical was applied at the rate of 10 pounds/acre (11.2 kg/ha) by drenching 46 ml of the 250 ppm solution on the surface of soil in 4½ inch (11.25 cm) plastic pots wherein seeds of the following weeds had been planted: velvetleaf (*Abutilon theophrasti medic*) (VL), jimsonweed (*Datura stramonium* L.) (JW), tall morning glory (*Ipomea purpurea* L. Roth) (TM), switchgrass (*Panicum virgatum* L.) (SG), barnyardgrass (*Echinochloa crusgalli* (L.) Beauv.) (BG), green foxtail (*Setria viridis* (L.), Beauv.) (GF). The percent control of the weeds compared to untreated checks was determined two weeks after treatment. TABLE III summarizes the results achieved with compounds formulated as indicated above, and the data clearly indicate the good to excellent herbicidal efficacy of compounds of this invention.

TABLE III

| | Preemergence Activity (Percent Control at 11.2 kg/ha) | | | | | |
|---|---|---|---|---|---|---|
| Cpd. No. | VL | JW | TM | BG | SG | GF |
| 1 | 80 | 60 | 100 | 100 | 100 | 100 |

Similar herbicidal results are achieved with Compound Numbers 2-8 when applied to weeds in a manner indicated in Example 4.

EXAMPLE 5

Retardation of Plant Growth

To illustrate the effectiveness of the described compounds as plant growth regulants, 600 mg of chemical were dissolved in a 10 ml organic solvent comprising acetone to which 30 mg of an emulsifying agent, "Tween 20" (trademark) (an ethoxylated sorbitan monolaurate), was added. This solution was diluted to 200 ml with distilled water, producing a 3000 ppm solution/suspension. By appropriate dilutions with distilled water, 1000 and 500 ppm solution/suspensions were prepared. The spray solution/suspensions were atomized with a DeVilbiss (trademark) No. 152 sprayer and wetted the foliage to the drip point of soybean plants (*Glycine max* (L.) Merr., cv. Williams, 2 weeks old), cotton plants (*Gossypium hirsutum* L. cv. Stoneville 213, 3-4 weeks old), bean plants (*Phaseolus vulgaris* L. cv. Pinto III, 2 weeks old), barley plants (*Hordeum vulgare* L. cv. Herta, 1 week old) and rice plants (*Oryza sativa* L. cv. Nato, 1 week old). After 1 to 3 weeks (depending on plant species) in a greenhouse, the plants were evaluated for retardation of vegetative growth. A summary of growth retardation data appears in Table IV.

TABLE IV

| | Percent Plant Growth Retardation | | | | |
|---|---|---|---|---|---|
| Cpd. No. | Barley 3000 ppm | Bean 1000 ppm | Cotton 3000 ppm | Soybean 3000 ppm | Rice 1000 ppm |
| 1 | 50 | 100 | —* | 100 | —* |

*—Indicates not tested

The above embodiments and examples illustrate the scope and spirit of the instant invention. These embodiments and examples will make apparent to those skilled in the art, other embodiments and examples within the scope of the present invention. Therefore, the instant invention should be limited only by the appended claims.

What is claimed:

1. A method for controlling weeds by applying to the locus where the control of weeds is desired a herbicidally effective amount of a compound having the formula:

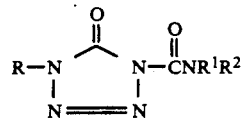

wherein R is:
  $C_1$-$C_4$ alkyl,
  phenyl, or
  phenyl substituted with at least one member of the group consisting of:
    $C_1$-$C_3$ alkyl and
    $C_1$-$C_3$ alkoxy;
$R^1$ is $C_1$-$C_4$ alkyl; and
$R^2$ is a radical having the formula:

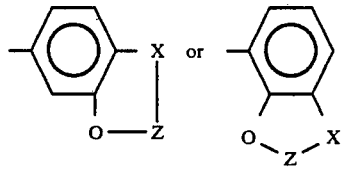

wherein X is oxygen or $CH_2$, and
  Z is $-CH_2-CH_2$ or $-CR^9R^{10}-$ wherein $R^9$ and $R^{10}$ are the same or different and are hydrogen or methyl.

2. A method in accordance with claim 1 wherein said weeds are controlled by applying said compound to the soil prior to the emergence of said weeds.

* * * * *